United States Patent
Vodinh

(10) Patent No.: US 9,757,146 B2
(45) Date of Patent: Sep. 12, 2017

(54) SCALPEL HANDLE HAVING A BLADE SHIELD UTILIZING OVER CENTER SPRING

(71) Applicant: Hien Vodinh, Knoxville, TN (US)

(72) Inventor: Hien Vodinh, Knoxville, TN (US)

(73) Assignee: Bosela Design LLC, Chattanooga, TN (US)

( * ) Notice: Subject to any disclaimer, the term of this patent is extended or adjusted under 35 U.S.C. 154(b) by 0 days.

(21) Appl. No.: 14/544,969

(22) Filed: Mar. 10, 2015

(65) Prior Publication Data

US 2015/0190165 A1 Jul. 9, 2015

Related U.S. Application Data

(63) Continuation-in-part of application No. 13/998,559, filed on Nov. 8, 2013, now Pat. No. 9,027,254.

(51) Int. Cl.
*A61B 17/3211* (2006.01)
*B26B 29/02* (2006.01)
*A61B 17/3213* (2006.01)

(52) U.S. Cl.
CPC ...... *A61B 17/3211* (2013.01); *A61B 17/3213* (2013.01); *B26B 29/02* (2013.01); *A61B 2017/32113* (2013.01)

(58) Field of Classification Search
CPC ............ A61B 17/3211; A61B 17/3213; A61B 2017/3213; A61B 2017/3211; B26B 29/04
USPC ............. 30/2, 151, 153, 161, 162, 294, 286; 606/167
See application file for complete search history.

(56) References Cited

U.S. PATENT DOCUMENTS

| 273,981 | A | * | 3/1883 | Glovers | B26B 1/04 30/153 |
| 942,342 | A | * | 12/1909 | mcnally | B26B 23/00 30/153 |
| 1,452,893 | A | * | 4/1923 | Porth | A22B 5/168 30/286 |
| 1,810,593 | A | * | 6/1931 | Brown | B26B 29/00 30/153 |
| 2,428,742 | A | * | 10/1947 | Rothe | C14B 5/04 69/17 |
| 3,457,383 | A | * | 7/1969 | Griffin | H01H 9/06 200/275 |
| 3,781,988 | A | * | 1/1974 | Jones | 30/2 |

(Continued)

*Primary Examiner* — Stephen Choi
*Assistant Examiner* — Fernando Ayala
(74) *Attorney, Agent, or Firm* — Michael E. McKee

(57) ABSTRACT

A scalpel handle for holding a blade includes a handle member and a blade shield for covering the cutting edge of the blade. The blade shield is connected to the handle member for movement relative thereto between a blade-covering position and an out-of-the-way position, and a finger-operable actuator is mounted upon the handle member for movement relative thereto and is connected to the shield so that by moving the actuator between first and second conditions, the shield is moved between its blade-covering and its out-of-the-way positions. An over center spring is interposed between the actuator and the handle member so that upon movement of the actuator into its second condition, the shield is biased into the out-of-the-way position and so that upon movement of the actuator into its first condition, the shield is biased into the blade-covering position.

14 Claims, 8 Drawing Sheets

(56) References Cited

U.S. PATENT DOCUMENTS

| | | | | |
|---|---|---|---|---|
| 4,006,868 A | * | 2/1977 | Hochradel | B65G 51/06 406/186 |
| 4,513,761 A | * | 4/1985 | Van Deursen | A45D 2/122 132/251 |
| 5,139,507 A | | 8/1992 | Dolgin et al. | |
| 5,440,814 A | * | 8/1995 | Hall | B26B 3/06 30/286 |
| 6,178,640 B1 | * | 1/2001 | Votolato | B26B 27/005 30/2 |
| 6,718,637 B1 | * | 4/2004 | Ortner | B26B 5/00 30/2 |
| 7,024,772 B1 | | 4/2006 | Shaver et al. | |
| 7,485,126 B2 | | 2/2009 | Adelman et al. | |
| 7,509,742 B2 | | 3/2009 | Votolato | |
| 7,810,241 B2 | * | 10/2010 | Pooler | A61B 17/3211 30/151 |
| 8,347,509 B2 | | 1/2013 | Votolato | |
| 8,671,578 B1 | * | 3/2014 | Frazer | B26B 1/08 30/151 |
| 9,027,254 B1 | * | 5/2015 | Vodinh | A61B 17/3211 30/151 |
| 2002/0188309 A1 | * | 12/2002 | Adelman | A61B 17/3213 606/167 |
| 2011/0119925 A1 | * | 5/2011 | Rohrbach | B26B 5/003 30/158 |
| 2012/0279071 A1 | | 11/2012 | Garavaglia et al. | |
| 2012/0317820 A1 | | 12/2012 | McGushion et al. | |
| 2013/0185943 A1 | | 7/2013 | Landwehr | |
| 2013/0326884 A1 | * | 12/2013 | Harvey | B26B 1/042 30/161 |
| 2014/0155202 A1 | * | 6/2014 | Young | F42B 6/08 473/583 |

\* cited by examiner

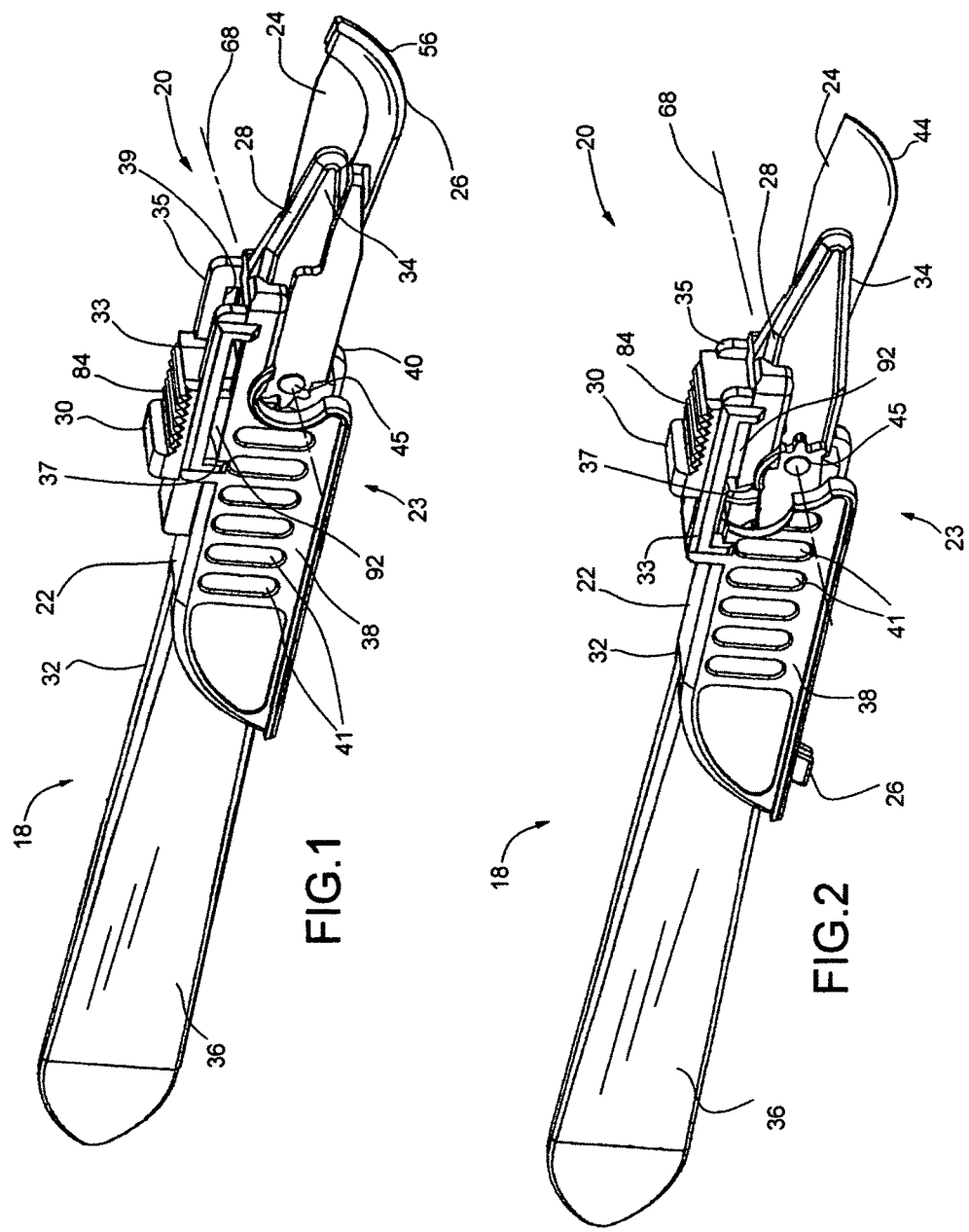

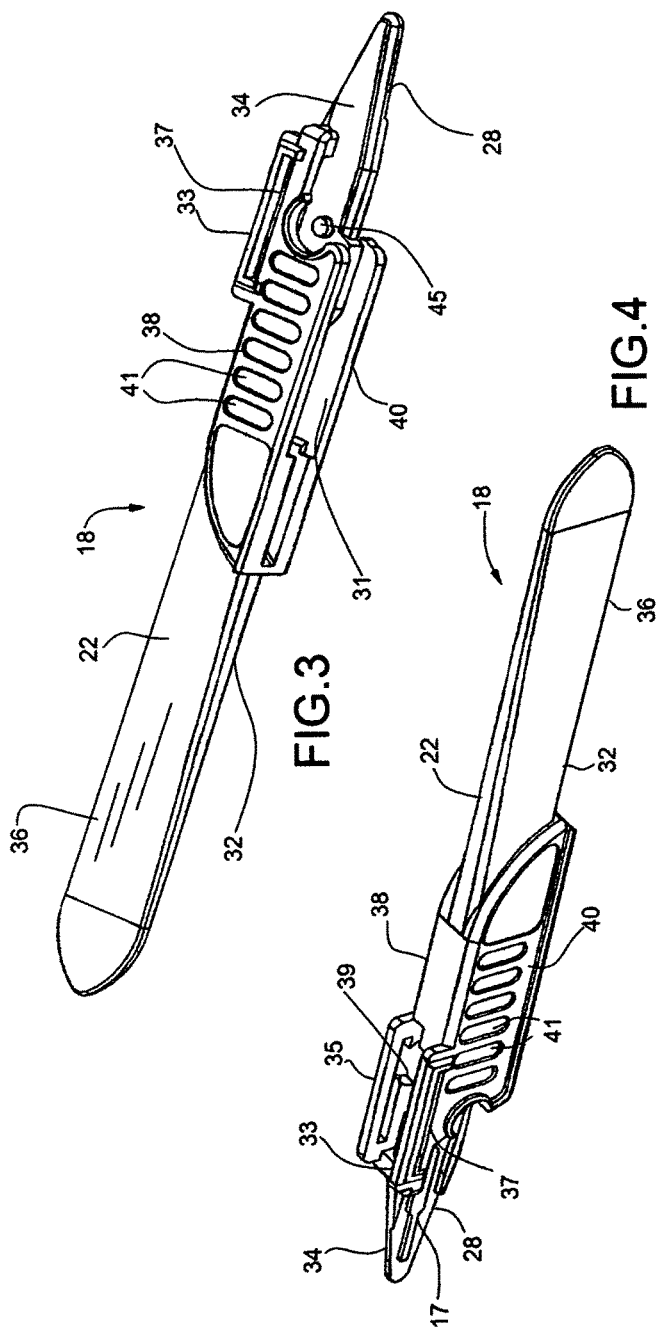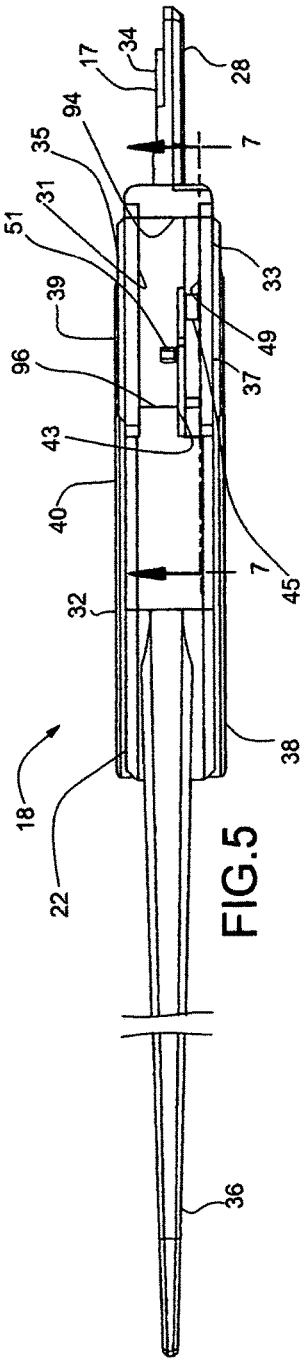

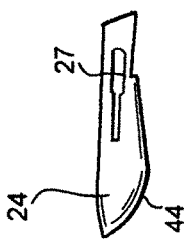
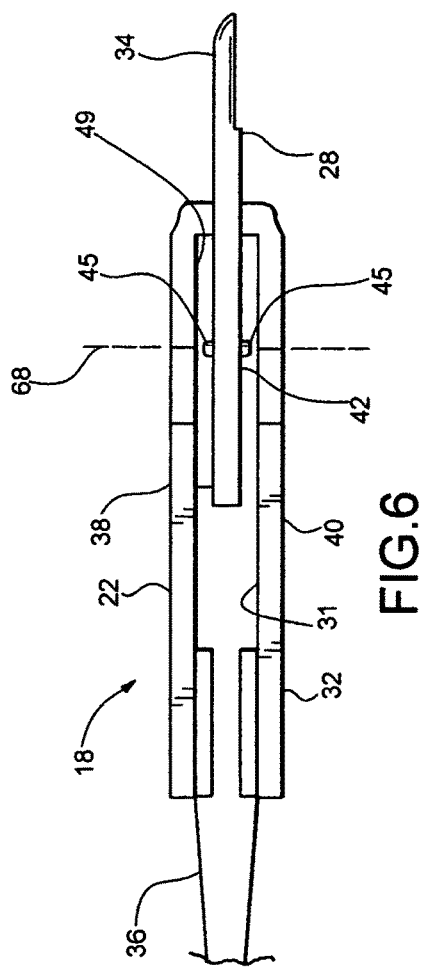
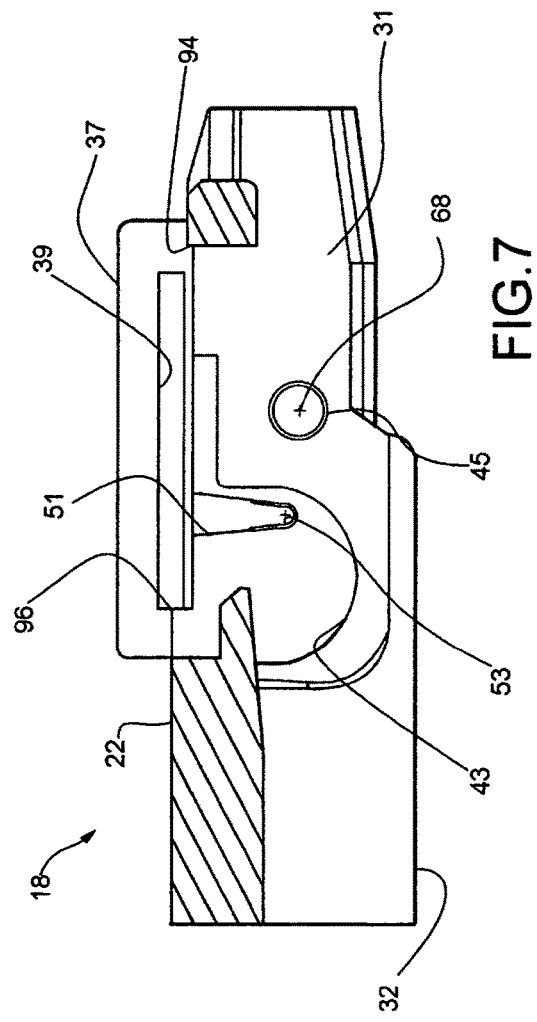

SCALPEL HANDLE HAVING A BLADE SHIELD UTILIZING OVER CENTER SPRING

This invention is a continuation-in-part of application Ser. No. 13/998,559, filed Nov. 8, 2013 and entitled SCALPEL HANDLE HAVING A BLADE SHIELD, the disclosure of which is incorporated herein by reference.

BACKGROUND OF THE INVENTION

This invention relates generally to surgical scalpels and relates, more particularly, to means and methods by which the cutting edge of a scalpel blade is covered between periods of use.

It is known that in order to reduce the risk of inadvertent cuts from a scalpel in a surgical environment as, for example, the scalpel is passed from one individual to another, the cutting blade of the scalpel can be covered with a safety shield between periods of use, and it is this class of shielded scalpels to which the present invention is to be compared. One such shielded scalpel is described in my co-pending U.S. Ser. No. 13/998,559 as having an elongated handle, a cutting blade which extends from the handle and a safety shield which is attached to the handle for movement relative thereto between a blade edge-covering position and an out-of-the way position at which the cutting edge of the blade is exposed for use. Furthermore, a manually-operable actuator mechanism is mounted upon the handle for manipulation of the actuator mechanism relative to the handle between first and second conditions, and other mechanisms (e.g. linkages) are interposed between the actuator mechanism and the safety shield so that the movement of the shield between its edge-covering and out-of-the-way positions is effected by the movement of the actuator mechanism relative to the handle between its first and second conditions.

A limitation associated with shielded scalpel designs of the prior art relates to the schemes by which the blade shields are held in place in each of its blade-covering position and its out-of-the-way position. In particular, such shielded scalpel designs commonly rely upon a closely-controlled fit-up between adjacent components of the scalpel design to ensure that the blade shield is maintained in each of its blade-covering position and its out-of-the-way position. In other words, if the fit-up between adjacent components of the scalpel design is too loose (resulting, for example, from tolerance error during manufacture of the scalpel components), the blade shield is not likely to be firmly held in its blade-covering position when the actuator mechanism is moved into its first condition and also be firmly held in its blade-covering condition when the actuator mechanism is moved to its second condition.

It would be desirable to provide a scalpel handle whose safety shield is urged into its blade-covering condition when the actuator mechanism is manually moved into its first condition and is urged into its out-of-the-way condition when the actuator mechanism is manually moved into its second condition.

Accordingly, it is an object of the present invention to provide a new and improved scalpel handle having a safety shield for covering the blade mounted upon the handle.

Another object of the present invention is to provide such a scalpel handle having a safety shield which is movable between a blade-covering position and an out-of-the-way position at which the cutting edge of the blade is exposed for use and which employs an improved scheme for firmly holding the shield in each of its blade-covering position and its out-of-the-way position.

Still another object of the present invention is to provide such a scalpel handle whose shield is urged into its blade-covering position when the actuator mechanism is moved toward the position assumed when in its first condition and is also urged into its out-of-the-way position when the actuator mechanism is moved toward the position assumed when in its second condition.

Yet another object of the present invention is to provide such a scalpel handle whose shield can be readily moved by an operator between its blade-covering and its out-of-the-way position.

A further object of the present invention is to provide such a scalpel handle having an actuator mechanism which can be manipulated by a finger (e.g. the index finger) of the hand which grasps the handle for moving the blade shield between its blade-covering position and its out-of-the-way position.

A still further object of the present invention is to provide such a scalpel handle whose actuator mechanism can be manipulated between first and second conditions for moving the blade shield between its blade-covering position and its out-of-the-way position and whose actuator mechanism is biased into the position assumed when in its first condition and is biased into the position assumed when in its second condition.

A yet further object of the present invention is to provide such a scalpel handle which is comprised of relatively few components.

One more object of the present invention is to provide such a scalpel handle which is uncomplicated in structure, yet effective in operation.

SUMMARY OF THE INVENTION

This invention resides in a scalpel handle for holding a blade having a cutting edge.

The scalpel handle includes a handle member to which a blade is securable for use and a blade shield for covering the cutting edge of the blade when the blade is secured to the handle member. In addition, the blade shield is connected to the handle member for pivotal movement relative thereto between a blade-covering position at which the blade shield covers the cutting edge of the blade and an out-of-the way position at which the cutting edge of the blade is exposed for use. The handle further includes a manually-operable actuator mechanism which is mounted upon the handle member for movement relative thereto between a first condition and a second condition, and the actuator mechanism is connected to the blade shield so that by manually moving the actuator mechanism from the first condition toward the second condition, the blade shield is moved from the blade-covering position toward the out-of-the-way position. Furthermore, the handle includes an over center spring interposed between the actuator mechanism and the handle member so that upon movement of the actuator mechanism from the first condition into the position assumed by the actuator mechanism when in the second condition, the blade shield is biased by the over center spring into the out-of-the-way position.

BRIEF DESCRIPTION OF THE DRAWINGS

FIG. 1 is a perspective view of a scalpel assembly within which features of the present invention are embodied and illustrating the blade shield of the assembly when disposed in a blade-covering position.

FIG. 2 is a perspective view of the FIG. 1 scalpel assembly similar to that of FIG. 1, but illustrating the blade shield of the assembly when disposed in an out-of-the-way position.

FIGS. 3 and 4 are alternative perspective views of the handle member of the FIG. 1 assembly.

FIG. 5 is a top plan view of the handle member of FIGS. 3 and 4.

FIG. 6 is a bottom plan view of a fragment of the handle member of FIGS. 3 and 4.

FIG. 7 is a cross-sectional view of a fragment of the hollow interior of the handle member of FIGS. 3 and 4 taken about along line 7-7 of FIG. 5.

FIG. 8 is a side elevation view of the blade utilized in the FIG. 1 assembly.

DETAILED DESCRIPTION OF AN ILLUSTRATIVE EMBODIMENT

Figure 9:
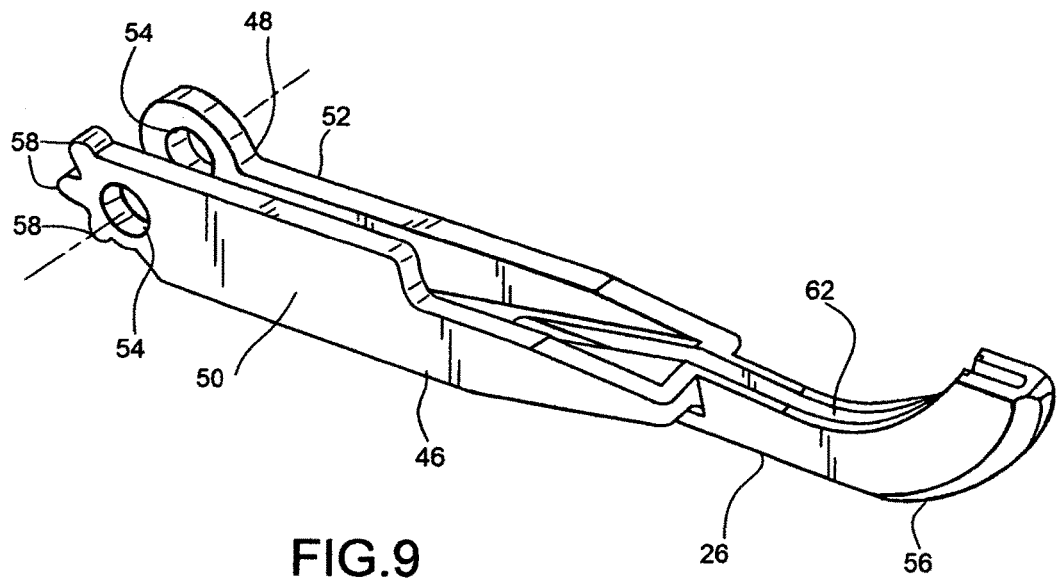
FIG. 9 is a perspective view of the blade shield of the FIG. 1 assembly.

Turning now to the drawings in greater detail and considering first FIGS. 1 and 2, there is illustrated an embodiment, generally indicated 20, of a scalpel, or scalpel assembly, within which features of the present invention are embodied. Briefly, the scalpel 20 includes means, generally indicated 18, providing a handle of the scalpel 20 and an elongated blade 24 which is connected to the handle-providing means 18. The handle-providing means 18 of the depicted scalpel 20 includes an elongated handle member 22 to which the elongated blade 24 is fixedly secured adjacent one (i.e. a forward) end of the handle member 22 and further includes a blade shield 26 which is joined to the handle member 22 for pivotal movement of the shield 26 relative to the handle member 22 between a first condition, or position, as illustrated in FIG. 1, at which the shield 26 covers, and thereby protects, the cutting edge of the blade 24 and a second condition, or position, as illustrated in FIG. 2, at which the shield 26 is moved to an out-of-the-way position against the underside (as viewed in FIG. 2) of the handle member 22 so that the cutting edge of the blade 24 is exposed for use.

The invention described herein can be embodied in both reusable or disposable scalpels. Accordingly, the principles of the present invention can be variously applied.

The scalpel 20 further includes a manually-operable actuator mechanism 30 which is joined to the handle member 22 for sliding movement relative thereto between a rearwardly-disposed (or first) condition, as illustrated in FIG. 1, and a forwardly-disposed (or second) condition, as illustrated in FIG. 2, and the actuator mechanism 30 is connected to the blade shield 26 so that movement of the actuator mechanism 30 from its FIG. 1 first condition toward its FIG. 2 second condition pivotally moves the blade shield 26 from its FIG. 1 blade-covering position to its FIG. 2 out-of-the-way position and so that movement of the actuator mechanism 30 from its FIG. 1 first condition toward its FIG. 2 second condition pivotally moves the blade shield 26 from its FIG. 2 out-of-the-way position to its FIG. 1 blade-covering condition.

The scalpel 20 also includes mechanical biasing means, generally indicated 23 in FIGS. 1 and 2, which is interposed between the actuator mechanism 30 and the handle member 22 for biasing the actuator mechanism 30 into its FIG. 1 first condition as the actuator mechanism 30 is moved from its FIG. 2 second condition and into relatively close proximity to the position assumed when the actuator mechanism 30 is positioned in its FIG. 1 first condition and for biasing the actuator mechanism 30 into its FIG. 2 second position as the actuator mechanism 30 is moved from its FIG. 1 first condition and into relatively close proximity to the position assumed when the actuator mechanism 30 is positioned in its FIG. 2 second condition. Because of the interconnection (described herein) between the actuator mechanism 30 and the blade shield 26, the resultant biasing of the actuator mechanism 30 into each of its first and second conditions as aforedescribed also biases the blade shield 26 into each of its FIG. 1 blade-covering and FIG. 2 out-of-the-way conditions so that the blade shield 26 is firmly held in place in each of its blade-covering and out-of-the-way conditions. As will be apparent and within the depicted scalpel 20, the mechanical biasing means 23 is in the form of an over center spring 25 (best shown in FIGS. 12-16) which is pivotally movable relative to each of the handle member 22 and the actuator mechanism 30 as the actuator mechanism 30 is moved relative to the handle member 22 between the FIG. 1 first condition and the FIG. 2 second condition.

With reference to FIGS. 3-7, the handle member 22 includes an elongated body 32 having opposite front and rear ends 34 and 36, respectively, and two opposite side portions 38 and 40 disposed medially of the front and rear ends 34 and 36. The handle member 22 is relatively thin as measured transversely of the body 32 through the opposite side portions 38 and 40 thereof and includes a forwardly-extending blade support 28 to which the blade 24 (FIGS. 1 and 2) is rigidly secured. Inasmuch as the scalpel 20 is intended to be grasped by an operator, or user, as the handle member 22 rests atop of the web of the hand which extends between the thumb and index finger of the grasping hand and the tips of the index finger and thumb of the grasping hand are positioned against the side portions 38 and 40 of the handle member 22 during use, it is preferred that the outer surfaces of the side portions 38 and 40 are provided with a plurality of recesses 41 disposed thereacross to both reduce the likelihood that the scalpel 20 will slip relative to the grasping hand during a surgical, or cutting, procedure and facilitate the manipulation of the handle member 22 during a cutting process performed with the scalpel 20. In addition, the outer surfaces of the side portions 38 and 40 can be roughened or textured to further reduce the likelihood of inadvertent slip of the handle member 22 within the operator's hand while still permitting the handle member 22 to be pivoted, as necessary, about the tips of the fingers and thumb of the grasping hand to alter the angular orientation of the handle member 22 during a cutting process.

In addition, the body 32 of the handle member 22 is provided with a downwardly-opening hollow interior 31 disposed between the side portions 38 and 40, a pair of parallel guide rails 33 and 35 which extend along the top of the handle member 22 adjacent the forwardly-extending blade support 28, and other formations which facilitate the attachment of other scalpel componentry to the handle member 22. In this regard, there is associated with the guide rails 33 and 35 a pair of elongated slots 37 and 39 which extend along the length of the rails 33, 35. As will be apparent herein, the actuator mechanism 30 is adapted to cooperate with the slots 37, 39 which is, in turn, serve as parallel guide tracks along which the actuator mechanism 30 is guided as it is moved linearly along the length of the guide rails 33, 35 between its FIG. 1 first and FIG. 2 second conditions.

As best shown in FIG. 6, the blade support 28 has a rearward portion 42 which is disposed centrally of the hollow interior 31 and is provided with a pair of aligned studs, or protuberances 45, which extend outwardly of the opposite sides of the blade support 28. As will be apparent herein, a bifurcated portion of the blade shield 28 is positioned about this rearward portion 42 and connected to the protuberances 45 for pivotally attaching the blade shield 28 to the handle member 22 which, in turn, permits the pivotal movement of the blade shield 28 relative to the handle member 22 about a pivot axis 68 which extends through the center of the protuberances 45. In addition, the hollow interior 31 opens out of the top of the handle member 22 through an elongated slot 49. As will be apparent herein, the actuator mechanism 30 and the blade shield 28 are connected to one another by way of, or through, this slot 49.

With reference again to FIGS. 5 and 7, the hollow interior 31 is sized to bodily accept the blade shield 26 when the blade shield 26 is pivotally moved about the pivot axis 68 to its out-of-the-way position. Furthermore, there is associated with the hollow interior 31 a cutout 43 (FIGS. 5, 7 and 19) which is adapted to accept the over center spring 25 when the spring 25 is mounted within the handle member 22 and which is sized to accommodate a readjustment in position, or orientation, of the spring 25 as the spring 25 is pivotally moved between two positions in response to the movement of the actuator mechanism 30 between its first and second conditions. The handle member 22 also defines a relatively shallow groove 51 which extends downwardly (as viewed in FIGS. 7 and 19) from the top of the handle member 22 and along the cutout 43, and this groove 51 accepts one end of the spring 25 when positioned within the handle member 22 during assembly of the scalpel 20. In addition, the groove 51 defines an abutment surface 53 adjacent the bottom thereof against which the accepted end of the spring 25 acts upon the handle member 22 during use of the scalpel 20.

If the handle member 22 of the scalpel 20 is not intended to be reused, the body 32 of the handle member 22 is preferably formed (e.g. molded) in one piece out of a hard plastic material, but other materials can be used. In the alternative and if the handle member 22 is intended to be reused, the handle member 22 is preferably constructed out of metal, such as stainless steel. In addition, the protuberances 45 (through which the pivot axis 68 extends) could be replaced by a single pin which extends through an appropriately-sized through-bore formed within the blade support 28.

As best shown in FIG. 8, the blade 24 of the scalpel 20 is elongated and relatively thin in shape and defines a relatively sharp cutting edge 44 which extends along one of its edges (i.e. the lower edge as viewed in FIG. 8). As is the case with common scalpel blades, the blade 24 defines an elongated slot 27 which is disposed medially of and extends along the blade body which enables the blade 24 to be secured to the blade support 28. To this end and for purposes of holding a replaceable blade 24, the blade support 28 (FIG. 5) is fashioned with a fitting 17 which is adapted to cooperate with the blade 24 in a manner which is well-known in the art to releasably attach the blade 24 to the blade support 28.

Suffice it to say that in order to secure the blade 24 to the support 28, the blade 24 is positioned against the blade support 28 so that the elongated slot 27 accepts the fitting 17 of the support 28 and so that the blade 24 is thereby rigidly secured to the handle member 22. If the scalpel handle 22 is constructed of plastic and not intended to be reused (i.e. intended to be discarded with the blade following its initial use), the slot 27 of the blade 24 could be first positioned about the fitting 17, and the fitting 17 can be subsequently heated to heat seal the blade 24 in place. The blade 24 is preferably constructed of metal, such as stainless steel, but other materials can be used.

Figure 10:
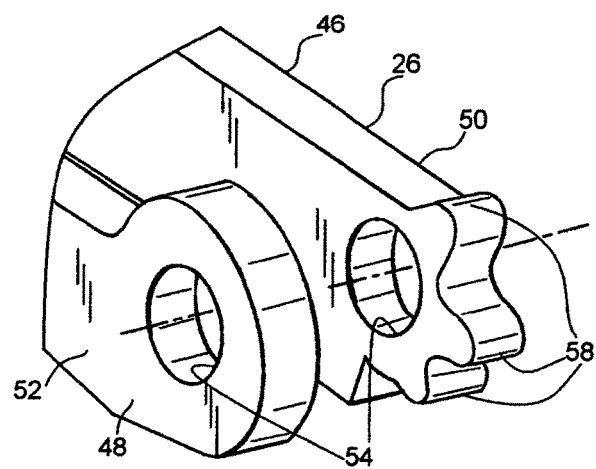
FIG. 10 is a perspective view of a fragment of the FIG. 9 blade shield, as seen from an alternative angle and drawn to a slightly larger scale.

With reference to FIGS. 9 and 10, the blade shield 26 includes an elongated body 46 having a bifurcated proximal portion 48 having a pair of prongs 50, 52 through which is defined an aligned pair of through-openings 54 with which the shield 26 is pivotally connected to the handle member 22 (by way of the aligned protuberances 45) and further has an elongated distal portion 56 which is joined to and extends from the proximal portion 48. One prong 50 of the proximal portion 48 also defines a series of gear teeth 58 which project from the end of the body 46 opposite the proximal portion 48. As will be apparent herein, the series of gear teeth 58 operatively connect the actuator mechanism 30 to the blade shield 26 so that movement of the actuator mechanism 30 relative to and along the handle member 22 between the FIG. 1 first and FIG. 1 second conditions effects the movement of the blade shield 26 between its FIG. 1 blade-covering and FIG. 2 out-of-the-way positions.

Meanwhile, the distal portion 56 is somewhat arcuate in shape as a path is traced along the length thereof and defines a blade-accepting groove 62 which extends therealong. The groove 62 is provided with a bottom whose shape is substantially complementary to the curvature of the blade cutting edge 44 so that when the shield 26 is positioned in its FIG. 1 blade-covering condition, the groove 62 accepts, and thereby covers, the blade cutting edge 44.

Figure 17:
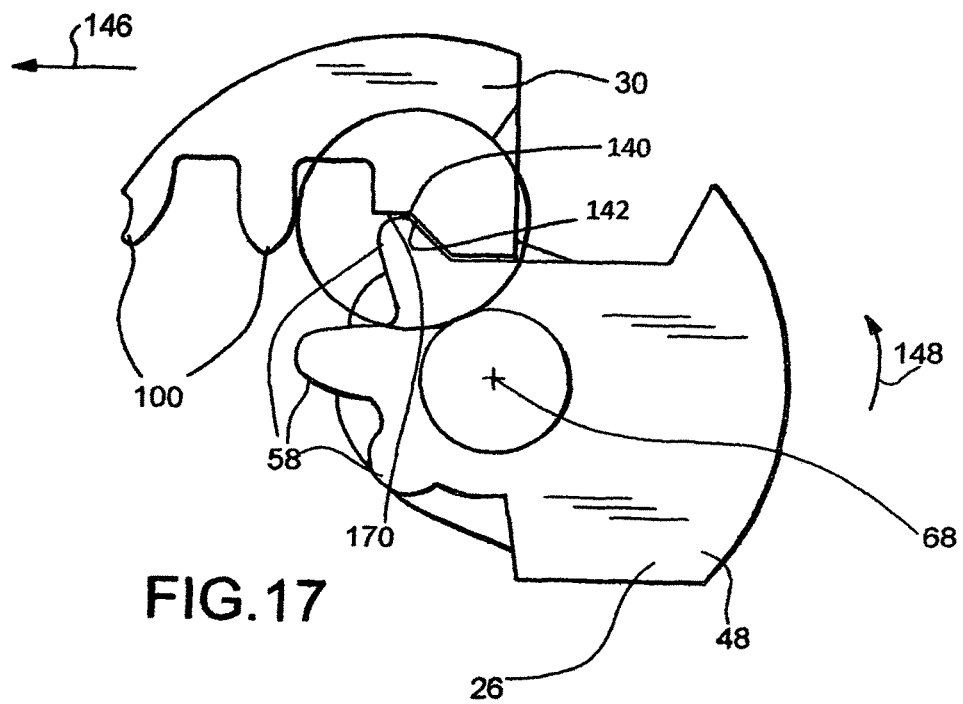
FIG. 17 is a view of the mating gear teeth of the actuator mechanism and the blade shield as seen within the circle A of FIG. 13 but drawn to a slightly larger scale.

To pivotally secure the shield 26 to the handle member 22 and with reference to FIG. 17, the prongs 50, 52 of the proximal portion 48 of the shield 26 are positioned within the hollow interior 31 of the handle member 22 and about the rearward portion 42 of the blade support 28 so that the pair of through-openings 54 are aligned with the protuberances 45 provided within the rearward portion 42, and then the through-openings 54 are manipulated onto, or about, the protuberances 45. If necessary, the prongs 50, 52 can be spread apart by a small amount to position the through-openings 54 about the protuberances 45. Once positioned about the protuberances 45, the inherent resiliency of the material (e.g. relatively hard plastic) comprising the blade shield 26 will retain the shield 26 about the protuberances 45.

It will be understood that with the blade shield 26 being secured to the handle member 22 as aforedescribed by way of the pair of protuberances 45, the shield 26 can be pivoted about the pivot axis 68 (FIGS. 1, 2 and 13-15) between the condition illustrated in FIG. 1 (and FIG. 13) at which the distal portion 56 of the blade shield 26 extends forwardly of the handle member 22 and the cutting edge 44 of the blade 24 is accepted by the groove 62 of the distal portion 56 and the condition illustrated in FIG. 2 (and FIG. 15) at which the distal portion 56 extends rearwardly of the front end 34 of the handle member 22 so that the distal portion 56 is disposed remote of the cutting edge 44. In other words, when the shield 26 is positioned in its FIG. 2 (and FIG. 15) out-of-the-way condition, the distal portion 56 is positioned against the underside of the handle member 22, and the cutting edge 44 of the blade 24 is exposed for use of the scalpel 20. Furthermore, it will be understood that the axis of pivot 68 about which the shield 26 is pivotally moved between its FIG. 1 and FIG. 2 conditions is oriented substantially normal to the longitudinal axis of the handle member 22, and as the shield 26 is moved between its FIG. 1 and FIG. 2 positions, the shield 26 moves through about 180 degrees of movement.

Figure 11:
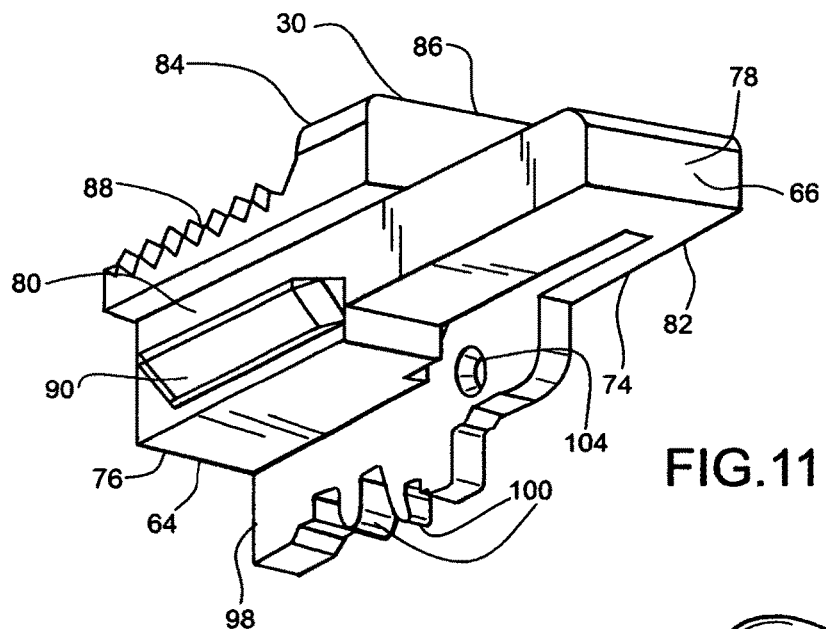
FIG. 11 is a perspective view of the actuator mechanism of the FIG. 1 assembly.

With reference to FIG. 11, the manually-operable actuator mechanism 30 of the scalpel assembly 20 includes an elongated body 74 having two opposite forward and rearward ends 76 and 78, respectively, and two opposite side surfaces 80, 82 which extend between the two ends 76, 78. The body 74 also includes a top portion 84 which is adapted to be engaged and acted upon by the index finger of the grasping hand of the user for manually sliding the actuator mechanism 30 forwardly or rearwardly relative to the handle member 22 between the FIG. 1 first condition and the FIG. 2 second condition. With this in mind, the top portion 84 is provided with an upwardly-disposed finger rest 86 and a grooved, or roughened, surface portion 88 which is intended to enhance the comfort of the user as the finger is pressed thereagainst and to reduce the likelihood of slip between the finger and the top portion 84 as the index finger is used to move the actuator mechanism 30 along the handle member 22.

Figure 19:
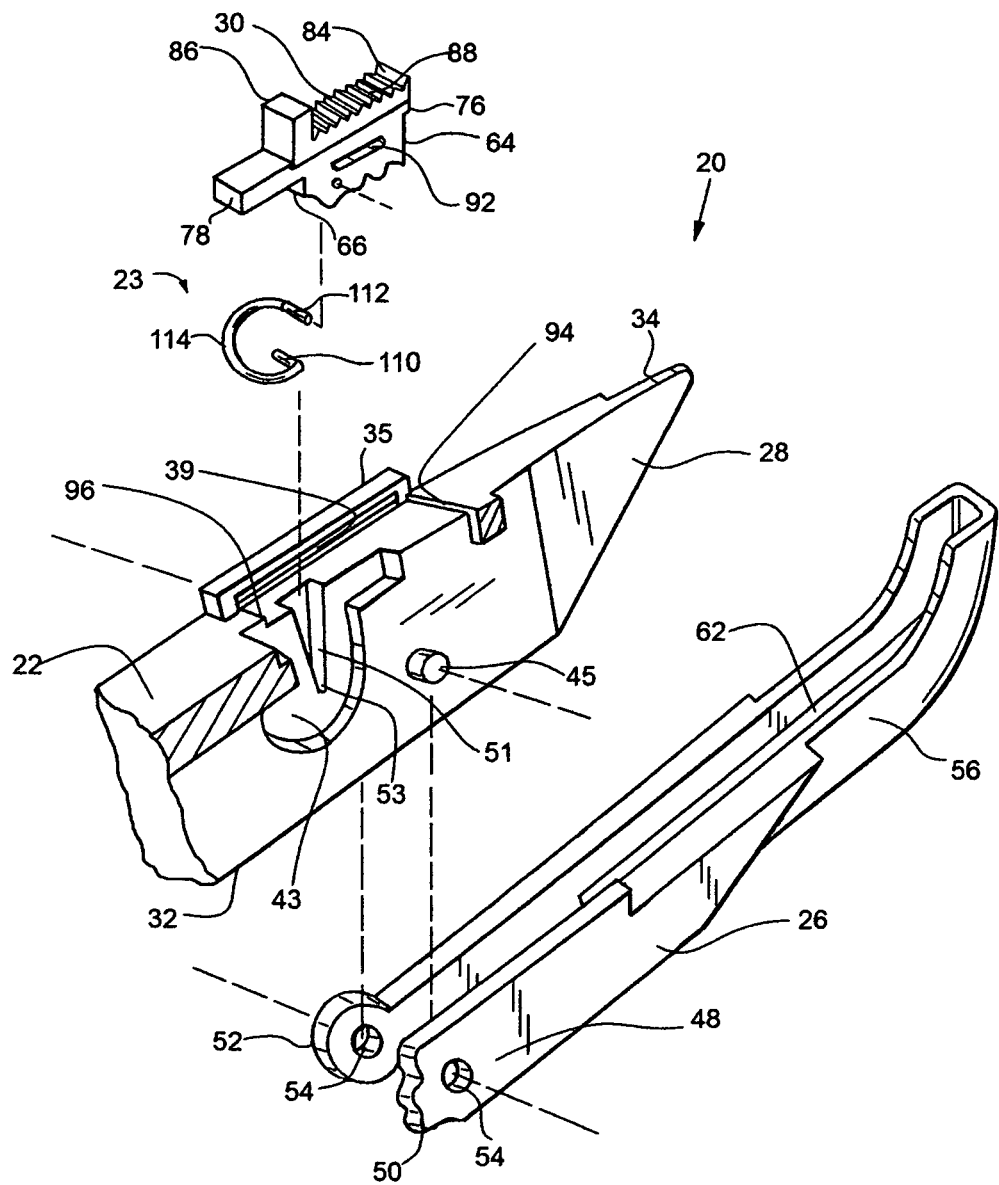
FIG. 19 is a perspective view schematically illustrating a fragment of the FIG. 1 assembly, shown exploded.

For purposes of joining the actuator mechanism 30 to the handle member 30 and with reference to FIGS. 11 and 19, the body 74 of the actuator mechanism 30 includes a pair of elongated tabs, or ribs 90, 92, which extend outwardly from the side surfaces 80, 82 and which are sized to be slidably accepted by the elongated slots 37, 39 (FIG. 4) associated with the guide rails 33, 35 disposed along the top of the handle member 22. More specifically, each rib 90 or 92 is sized to be accepted by a corresponding elongated slot 37 or 39 for movement therealong between the opposite ends of the slot 37 or 39. Therefore and as the actuator mechanism 30 is manually moved forwardly or rearwardly relative to the handle member 22, the ribs 90, 92 slidably move along the length of the elongated slots 37, 39 so that the movement of the actuator mechanism 30 is thereby guided along a linear path as the actuator mechanism 30 is moved between the forward and rearward ends of the elongated slots 37, 39.

Upon movement of the actuator mechanism 30 forwardly along the handle member 22 to its FIG. 2 second condition therealong, a forwardly-facing abutment surface 64 defined on the actuator mechanism 30 abuts a corresponding abutment surface 94 (FIGS. 5 and 7) provided on the handle member 22 adjacent the forward end of the guide rails 33, 35 to thereby limit the travel of the actuator mechanism 30 forwardly along the handle member 22. Similarly, upon movement of the actuator mechanism 30 rearwardly along the handle member 22 to its FIG. 1 first condition therealong, a rearwardly-facing abutment surface 66 defined on the actuator mechanism 30 abuts a corresponding abutment surface 96 (FIGS. 5 and 7) provided on the handle member 22 adjacent the rearward end of the guide rails 33, 35 to thereby limit the travel of the actuator mechanism 30 rearwardly along the handle member 22. It will therefore be understood, however, that the instant that the blade shield 26 comes to rest against the blade edge 44 when moved into its FIG. 1 blade-covering position (from the FIG. 2 out-of-the-way position) coincides with the instant that the abutment surfaces 64 and 94 are moved into abutting engagement with one another, and that the instant that the blade shield 26 comes to rest against the underside of the handle member 22 when moved into its FIG. 2 out-of-the-way position (from the FIG. 1 blade-covering position) coincides with the instant that the abutment surfaces 66 and 96 are moved into abutting engagement with one another.

As an alternative to utilizing the cooperating pairs of abutment surfaces 64, 94 and 66, 96 to halt the movement of the actuator mechanism 30 forwardly and rearwardly along the length of the handle member 22, alterations can be made to the length of the ribs 90, 92 which extend along the side surfaces 80, 82, respectively, of the actuator mechanism 30 so that the forward and rearward movement of the actuator mechanism 30 along the length of the handle member 22 can be halted upon movement of the ribs 90, 92 into abutting relationship with the ends of the elongated slots 37, 39. In other words, by lengthening the ribs 90, 92 at each of its opposite ends, the forward movement of the actuator mechanism 30 along the handle member 22 can be halted when the forward ends of the ribs 90, 92 move into abutting relationship which the forward ends of the slots 37, 39, and the rearward movement of the actuator mechanism 30 along the handle member 22 can be halted when the rearward ends of the ribs 90, 92 move into abutting relationship with the rearward ends of the slots 37, 39.

As mentioned earlier, the actuator mechanism 30 and blade shield 26 are connected to one another so that manual movement of the actuator mechanism 30 forwardly and rearwardly along the handle member 22 between its FIG. 1 first condition and its FIG. 2 second condition effects the pivotal movement of the blade shield 26 between its FIG. 1 blade-covering position and its FIG. 2 out-of-the-way position. To this end, the elongated body 74 of the actuator mechanism 30 includes a connection portion 98 which extends downwardly (as viewed in FIG. 11) from the remainder of the body 74. This connection portion 78 defines a series of downwardly-depending gear teeth 100 (FIG. 10) which are adapted to mesh with the series of gear teeth 58 provided on the proximal portion 48 of the blade shield 26 so that movement of the actuator mechanism 30 along the handle member 22 effects a corresponding movement of the blade shield 26 about the pivot axis 68.

Figure 13:
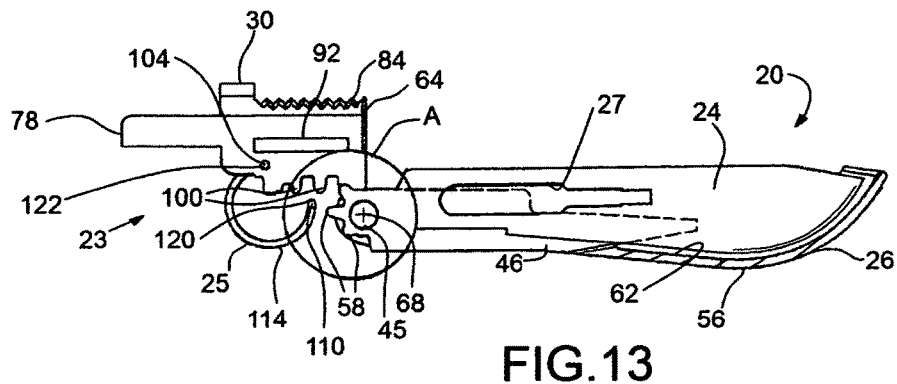
FIGS. 13-15 are side elevation views, shown partially in cross section, of various components of the FIG. 1 assembly schematically illustrating, in sequential views, the positional relationship of the actuator mechanism and the blade shield of the FIG. 1 assembly as the actuator mechanism is manually moved along the handle member from a first condition to a second condition to effect the movement of the blade shield from a blade-covering position to an out-of-the-way position.
Figure 14:
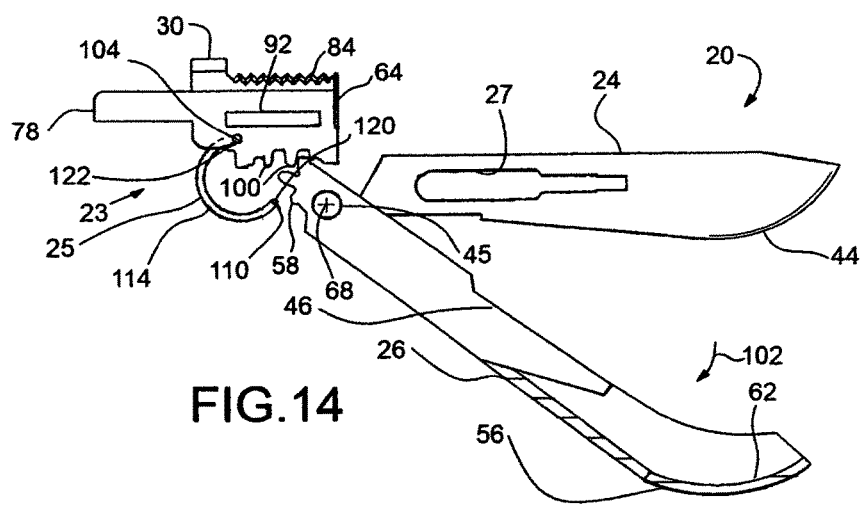
Figure 15:
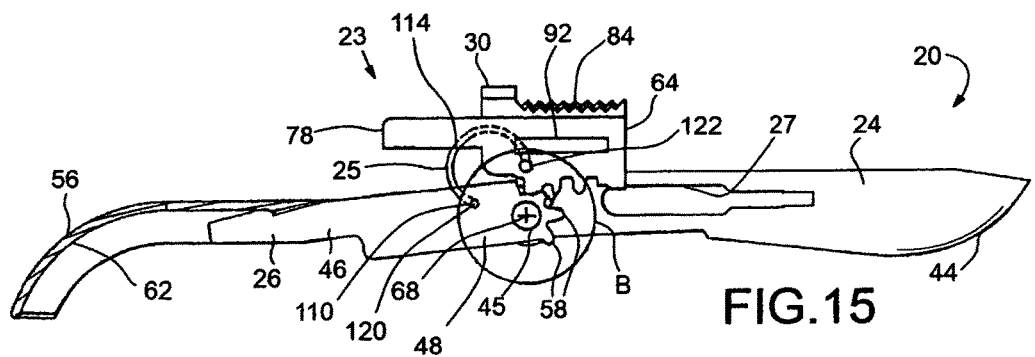

In connection with the foregoing and with reference to FIGS. 13-15, the gear teeth 58 and 100 of the blade shield 26 and actuator mechanism 30 are disposed within and mesh with one another through the elongated slot 49 (FIGS. 5 and 6) of the handle member 22 and are appropriately shaped so that as the actuator mechanism 30 is moved linearly along the handle member 22 from the FIG. 1 (and FIG. 13) first condition to the FIG. 2 (and FIG. 15) second condition, the blade shield 26 is rotated, or pivoted, (by way of the meshed gear teeth 58 and 100) about the pivot axis 68 and in the direction of the FIG. 14 arrow 102 from the FIG. 1 (and FIG. 13) blade-covering position to the FIG. 2 (and FIG. 15) out-of-the-way position and so that as the actuator mechanism 30 is moved linearly along the handle member 22 from the FIG. 2 (and FIG. 15) second condition to the FIG. 1 (and FIG. 13) first condition, the blade shield 26 is rotated, or pivoted, (by way of the meshed gear teeth 58 and 100) about the pivot axis 68 from the FIG. 2 (and FIG. 15) out-of-the-way position to the FIG. 1 (and FIG. 13) blade-covering position.

With reference again to FIG. 10, the connection portion 98 of the actuator mechanism 30 also includes a transversely-extending through-bore 104 disposed medially of the body 74 whose purpose will be apparent herein.

Figure 12:
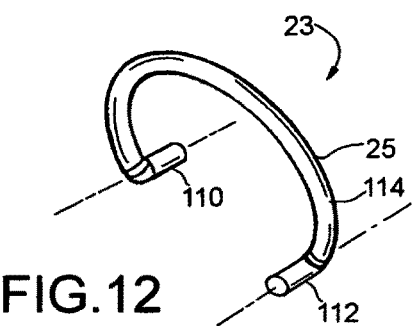
FIG. 12 is a perspective view of the over center spring utilized in the FIG. 1 assembly.
Figure 16:
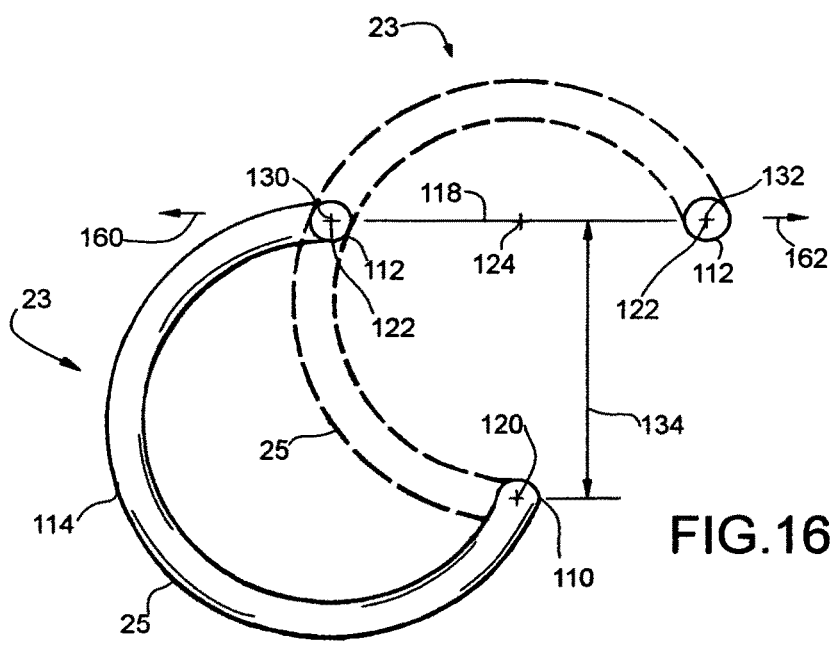
FIG. 16 is a side elevation view illustrating the adjustment in bodily orientation of the over center spring of FIG. 12 when the actuator mechanism of the FIG. 1 assembly is moved from the first condition to the second condition.

With reference to FIGS. 12 and 16, the over center spring 25 has two opposite end portions 110, 112 and a major portion 114 which extends along a C-shaped arcuate path between the end portions 110, 112 and which lies substantially in a single plane. Furthermore and for purposes of connecting the spring end portions 110, 112 between the actuator mechanism 30 and the handle member 22, each end portion 110 or 112 is linear in form and extends away from (i.e. normal to) the plane within which the major portion 114 of the spring 25 is contained and in a direction opposite the direction in which the other end portion 112 or 110 extends. For connection of the spring 25 to the handle member 22, one spring end portion 110 is positioned within the bottom of the groove 51 (FIG. 7) of the handle member 22 and against the abutment surface 53 defined therein, and the other spring end portion 112 (endwise) is accepted by the bore 104 (FIG. 11) provided in the connector portion 98 of the actuator mechanism 30.

With reference to FIG. 19, the blade shield 26 is connected to the handle member 22 by manipulating the prongs 50, 52 of the blade shield 26 over the protuberances 45 of the handle member 22 so that the protuberances 45 are accepted by the aligned through-openings 54 defined in the prongs 50, 52. One end portion 112 of the spring 25 is then inserted endwise into (and held therein) the bore 104 of the actuator mechanism 30, and then the actuator mechanism 30 is moved downwardly (as viewed in FIG. 19) toward the guide rails 33, 35 while the other end portion 110 is guided downwardly along the groove 51 (and into engagement with the abutment surface 53) while the C-shaped major portion 114 of the spring 25 is directed downwardly along the surface of the cutout 43. When the actuator mechanism 30 has been moved downwardly atop the guide rails 33, 35 (so that the gear teeth 100 are disposed in vertical registry with the slot 49 defined in the handle member 22 and the actuator mechanism 30 is substantially centered between the guide rails 33, 35, the actuator mechanism 30 can be pressed downwardly against the guide rails 33, 35 so that the elongated ribs 90, 92 spread the guide rails 33, 35 apart and are thereafter accepted by the elongated slots 37, 39 of the handle member 22 (into a snap-fit relationship therewith) to thereby attach the actuator mechanism 30 to the handle member 22. With the spring 25 thereby confined laterally with respect to the handle member 22 between the surface of the cutout 43 and the prong 50 of the blade shield 26, the spring end portion 112 is prevented from backing out of the bore 104 of the actuator mechanism 30.

The position of the blade shield 26 about the pivot axis 68 is taken into account before the actuator mechanism 30, or more specifically, the ribs 90, 92, are pressed into place along the slots 37, 39 so that the gear teeth 58 and 100 properly mesh with one another when the actuator mechanism 30 is thereafter moved along the slots 37, 39 between the FIG. 1 first condition and the FIG. 2 second condition. For example, if the blade shield 26 is disposed in its FIG. 1 blade-covering position during assembly of the scalpel 20 so that the gear teeth 58 are disposed rearwardly of the handle member 22 (with respect to the protuberances 45), the actuator mechanism 30 should be pressed downwardly into place adjacent the forward ends of the slots 37, 39. This way, the gear teeth 100 of the handle member 22 will desirably be disposed forwardly of the gear teeth 58 of the blade shield 26, as best shown in FIG. 15. In the alternative, if the blade shield 26 is disposed in its FIG. 2 out-of-the-way position during assembly of the scalpel 20 so that the gear teeth 58 are disposed forwardly of the handle member 22 (with respect to the protuberances 45), the actuator mechanism 30 should be pressed into place along the rearward ends of the slots 37, 39 so that the gear teeth 100 of the handle member 22 will desirably be disposed rearwardly of the gear teeth 58 of the blade shield 26, as best shown in FIG. 13.

With the actuator mechanism 30 connected to the handle member 22 as aforedescribed so that the over center spring 25 is interposed between the actuator mechanism 30 and the handle member 22, the spring 25 is in a compressed condition so that its end portions 110 and 112 are continually biased apart. Accordingly, the spring 25 is sized so that when positioned with its end portion 110 disposed within the bottom of the groove 51 (and engaging the abutment surface 53 thereof) and its other end portion 112 accepted (endwise) by the through-bore 104 of the actuator mechanism 30, the spring end portions 110 and 112 are continually urged further apart. This being the case, there is illustrated in FIGS. 13-15 the relative disposition of the spring 25, the actuator mechanism 30 and the blade shield 26 as the actuator mechanism 30 is moved along the handle member 22 between the FIG. 1 (and FIG. 13) first condition and the FIG. 2 (and FIG. 15) second condition. Within FIGS. 13-15, one spring end portion 110 (positioned in engagement with the abutment surface 53 disposed adjacent the bottom of the FIG. 19 groove 51) is adapted to pivot relative to the handle member 22 about a pivot axis, indicated 120 in FIGS. 13-15, while the other spring end portion 112 (accepted by the through-bore 104 of the actuator mechanism 30) is adapted to pivot relative to the handle member 22 about a pivot axis, indicated 122 in FIGS. 13-15. It therefore follows that as the actuator mechanism 30 is moved relative to the handle member 22 and linearly along the slots 37, 39, the pivot axis 122 is moved, or guided, linearly along a path of travel as the pivot axis 120 remains stationary within the handle member 22 and the C-shaped major portion 114 of the spring 25 is bodily rotated about the pivot axis 120.

As an aid to understanding the function of the over center spring 25 within the scalpel 20, there is illustrated in solid lines in FIG. 16 the disposition, or orientation, of the spring 25 in relation to the pivot axes 120, 122 when the actuator mechanism 30 is disposed in its FIG. 1 (and FIG. 13) first condition and there is illustrated in phantom in FIG. 16 the disposition, or orientation, of the spring 25 in relation to the pivot axes 120, 122 when the actuator mechanism 30 is disposed in its FIG. 2 (and FIG. 15) second condition. In this FIG. 16 view, the location of the pivot axis 122 when the actuator mechanism 30 is disposed in its FIG. 1 condition also corresponds with the location of the spring end portion 112 when the actuator mechanism 30 is disposed at its rearwardmost limit of travel along the length of the slots 37, 39, and this rearwardmost location of travel of the pivot axis 122 is indicated 130 in FIG. 16. By comparison, the location of the pivot axis 122 when the actuator mechanism 30 is disposed in its FIG. 2 second condition also corresponds with the location of the spring end portion 112 when the actuator mechanism 30 is disposed in its forwardmost limit of travel along the length of the slots 37, 39, and this forwardmost limit of travel of the pivot axis 122 is indicated 132 in FIG. 16. The path of travel of the pivot axis 122 between its rearwardmost and forwardmost limit of travel 130, 132 is indicated 118 in FIG. 16, and the midpoint of the path of travel 118 (i.e. the point located substantially halfway along the length of the path of travel 118) is indicated 124.

As mentioned earlier, the over center spring 25 is in a compressed condition when mounted in an assembled scalpel 20, and such a compressed condition continually urges the opposite end portions 110, 112 of the spring 25 apart. Since the spring end portion 110 remains in a fixed position against the abutment surface 53 of the handle member 22 as the actuator mechanism 30 is moved between the FIG. 1 first and the FIG. 2 second conditions, the only movement of the spring end portions 110 and 112 toward and away from one another is effected as the spring end portion 112 travels with the actuator mechanism 30 along the path of travel 118 between the forward and rearward limits of travel 130, 132. Moreover and due to the disposition of the spring end portion 110 relative to the path of travel 118, the closest that the pivot axis 122 ever gets to the pivot axis 120 is when the pivot axis 122 moves to the midpoint 124 of the path of travel 118. Stated another way, the closest that the pivot axis 122 ever gets to the pivot axis 120 corresponds with the distance, indicated 134 in FIG. 16, as measured between the pivot axis 120 and the midpoint 124 of the path of travel 118. Consequently, when the pivot axis 122 is positioned at any point rearwardly along the path of travel 118 from the midpoint 124 to the rearwardmost limit of travel 130, the urging apart of the spring end portions 110, 112 due to the compressed condition of the spring 25 induces a force component along the path of travel 118 which is directed rearwardly therealong (i.e. in the direction of the FIG. 16 arrow 160)) and, in turn, urges the actuator mechanism 30 rearwardly (with respect to the handle member 22) along the path of travel 118. By comparison, when the pivot axis 122 is positioned at any point forwardly along the path of travel 118 from the midpoint 124 to the forwardmost limit of travel 132, the urging apart of the spring end portions 110, 112 due to the compressed condition of the spring 25 induces a force component along the path of travel 118 which is directed forwardly therealong (i.e. in the direction of the FIG. 16 arrow 162)) and, in turn, urges the actuator mechanism 30 forwardly (with respect to the handle member 22) along the path of travel 118.

It therefore follows that the over center spring 25 is adapted to act between the actuator mechanism 30 and the handle member 22 so that until the actuator mechanism 30 has been moved forwardly with respect to the actuator mechanism 30 from the FIG. 1 first condition toward the FIG. 2 second condition along the path of travel 118 to about the midpoint 124 thereof (i.e. so that the pivot axis 122 is moved from the FIG. 16 location 130 to the midpoint 124), the movement of the blade shield 26 toward the FIG. 2 out-of-the-way position is opposed by the biasing force of the over center spring 25, but upon movement of the actuator mechanism 30 from the FIG. 1 first condition toward the FIG. 2 second condition along the path of travel 118 beyond the midpoint 124 thereof (i.e. so that the pivot axis 122 is moved from the midpoint 124 to the FIG. 16 location 132), the blade shield 26 is biased toward the FIG. 2 out-of-the-way position by the biasing force of the over center spring 25. Similarly, until the actuator mechanism 30 has been moved rearwardly with respect to the actuator mechanism 30 from the FIG. 2 second condition toward the FIG. 1 first condition along the path of travel 118 to about the midpoint 124 thereof (i.e. so that the pivot axis 122 is moved from the FIG. 16 location 132 to the midpoint 124), the movement of the blade shield 26 toward the FIG. 1 blade-covering position is opposed by the biasing force of the over center spring 25, but upon movement of the actuator mechanism 30 from the FIG. 2 second condition toward the FIG. 1 first condition along the path of travel 118 beyond the midpoint 124 thereof (i.e. so that the pivot axis 122 is moved from the midpoint 124 to the FIG. 16 location 130), the blade shield 26 is biased toward the blade-covering position by the biasing force of the over center spring 25.

An advantage provided by the scalpel 20 and its over center spring 25 relates to the maintenance of the blade shield 26 in each of its FIG. 1 blade-covering position and its FIG. 2 out-of-the-way position. More specifically, because the spring 25 continually biases, or urges, the distal portion 56 of the blade shield 26 upwardly (as viewed in FIG. 1) against the blade edge 44 when the actuator mechanism 30 is positioned in its FIG. 1 first condition and continually biases, or urges, the distal portion 56 of the blade shield 26 upwardly (as viewed in FIG. 2) against the underside of the handle member 22 when the actuator mechanism 30 is positioned in its FIG. 2 second condition, the likelihood is reduced that the distal portion 56 of the blade shield 26 will become dislodged or unintentionally fall downwardly from its FIG. 1 position against the blade cutting edge 44 or become dislodged or unintentionally fall downwardly from its FIG. 2 position against the underside of the handle member 22. Along the same lines and because the biasing force of the spring 25 continually acts upon the actuator mechanism 30 while the actuator mechanism 30 is positioned in either of its FIG. 1 first or FIG. 2 second conditions, the actuator mechanism 30 is firmly maintained in its first or second conditions by the spring 25 until such time that the operator desires to manually move (by way of the actuator mechanism 30) the blade shield 26 to the other of its blade-covering or out-of-the-way positions.

The aforedescribed advantage is further enhanced within the scalpel assembly 20 by the cooperating surfaces of the gear teeth 58 and 100 which engage one another when the blade shield 26 is positioned in each of its FIG. 1 (or FIG. 13) blade-covering position or its FIG. 2 (or FIG. 15) out-of-the-way position. More specifically and with reference to FIG. 17, there is illustrated engagement surfaces, indicated 142 and 140 of the gear teeth 58 and 100, respectively, which engage one another when the actuator mechanism 30 is positioned in its FIG. 1 first condition. When positioned in this FIG. 1 first condition, the spring 25 (FIGS. 12 and 15) biases the actuator mechanism 30 relative to the handle mechanism 30 in the direction of the FIG. 17 arrow 146 so that the blade shield 26 is continuously urged about the pivot axis 68 (and relative to the handle member 22) in the direction of the FIG. 17 arrow 148 and thus into engagement with the blade edge 44. Inasmuch as the engagement surface 142 is urged (by the biasing forces of the spring 25) against the engagement surface 140 in the FIG. 17 view, it follows that the engagement surfaces 142 and 140 cooperate as cam and cam follower, respectively, at the forward (or FIG. 2 second) limit of travel of the actuator mechanism 30 along the elongated slots 37, 39 (i.e. along the path of travel 118) to continuously urge the blade shield 26 about the pivot axis 68 in the direction of the FIG. 17 arrow 148.

Figure 18:
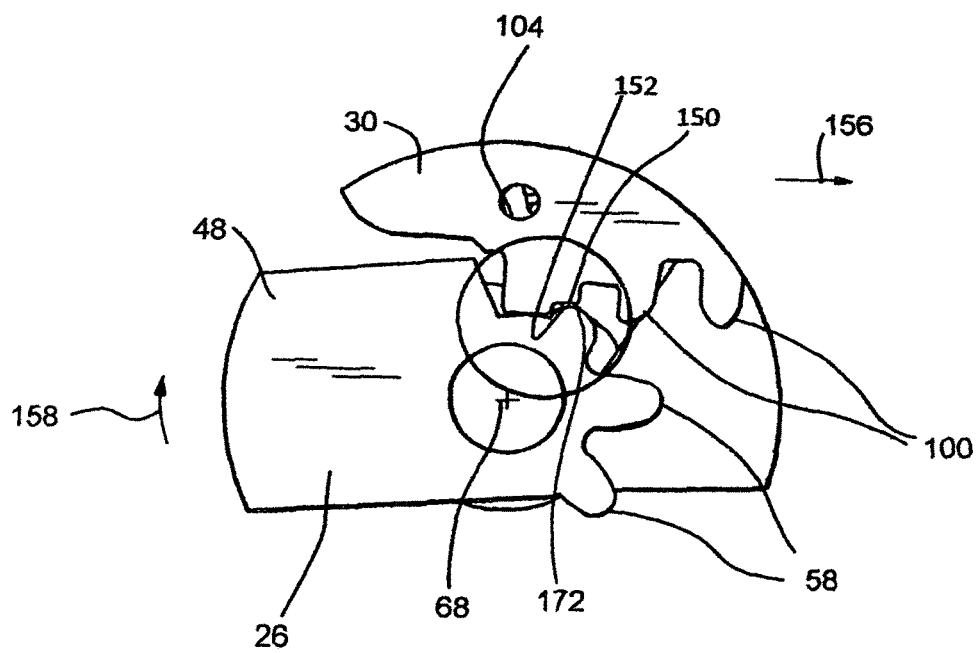
FIG. 18 is a view of the mating gear teeth of the actuator mechanism and the blade shield as seen within the circle B of FIG. 15 but drawn to a slightly larger scale.

Along similar lines and with reference to FIG. 18, there is illustrated engagement surfaces, indicated 152 and 150, of the gear teeth 58 and 100, respectively, which engage one another when the actuator mechanism 30 is positioned in its FIG. 2 second condition. When positioned in this FIG. 2 second condition, the spring 25 (FIGS. 12 and 15) biases the actuator mechanism 30 relative to the handle mechanism 22 in the direction of the FIG. 18 arrow 156 so that the blade shield 26 is continuously urged about the pivot axis 68 (and relative to the handle member 22) in the direction of the FIG. 18 arrow 158 and thus into engagement with the underside of the handle member 22. Inasmuch as the engagement surface 152 is urged (by the biasing forces of the spring 25) against the engagement surface 150 in the FIG. 18 view, it follows that the engagement surfaces 152 and 150 cooperate as cam and cam follower, respectively, at the rearward (or FIG. 1 first) limit of travel of the actuator mechanism 30 along the elongated slots 37, 39 (i.e. along the path of travel 118) to continuously urge the blade shield 26 about the pivot axis 68 in the direction of the FIG. 18 arrow 158.

Associated with the aforedescribed cooperating pairs of engagement surfaces 140, 142 and 150, 152 are flat surfaces which resists the manual movement of the blade shield 26 out of either of its blade-covering position or its out-of-the-way position if the distal portion 56 of the blade shield 26 were attempted to be manually moved downwardly (as viewed in FIGS. 13 and 15) about the pivot axis 68. More specifically and with reference to FIG. 17, there is associated with the gear teeth 100 a flat surface 170 located adjacent the surface 142 which is disposed directly above the uppermost gear tooth 58. If the distal portion 56 were to be urged downwardly about the pivot axis 68 (i.e. in the direction opposite the FIG. 17 arrow 148), the uppermost tooth 58 would exert a force against the flat surface 170 which would be absent a directional component which would urge the actuator mechanism 30 rearwardly along the length of the handle member 22. Similarly and with reference to FIG. 18, there is associated with the gear teeth 100 a flat surface 172 located adjacent the surface 152 which is disposed directly above the uppermost gear tooth 58. If the distal portion 56 were to be urged downwardly about the pivot axis 68 (i.e. in the direction opposite the FIG. 18 arrow 158), the uppermost tooth 58 would exert a force against the flat surface 172 which would be absent a directional component which would urge the actuator mechanism 30 forwardly along the length of the handle member 22. Therefore, the flat surfaces 170, 172 resist any attempted manual movement of the blade shield 26 out of its blade-covering and out-of-the-way positions and thereby help to lock the blade shield 26 in these positions.

Another advantage provided by the scalpel 20 relates to the amount of finger displacement required by operator to manually move the actuator mechanism 30 between the FIG. 1 first condition and the FIG. 2 second condition. In this regard and as mentioned earlier, upon movement of the actuator mechanism 30 along the path of travel 118 (FIG. 16) beyond the midpoint, the biasing force of the spring 25 biases (and thereby aids the movement of) the actuator mechanism 30 in the corresponding (e.g. desired) direction of movement along the path of travel 118. In practice, the biasing force of the spring 25 has been found to be of sufficient strength to automatically move the actuator mechanism 20 toward the desired FIG. 1 first or FIG. 2 second condition without aid of the operator's finger—once the actuator mechanism 30 has been moved beyond the midpoint 124 of the path of travel 118. Therefore and to move the blade shield 26 to either its FIG. 1 blade-covering position or its FIG. 2 out-of-the-way position, the operator need only move the actuator mechanism 30 from the FIG. 1 first or FIG. 2 second condition along the path of travel to a point just beyond the midpoint 124 thereof, because at that point, the biasing force of the spring 25 is sufficient to continue the movement of the actuator mechanism 30 to the desired first or second condition. Accordingly and to move, or flip, the blade shield from one of its blade-covering or out-of-the-way conditions to the other of its blade-covering or out-of-the-way conditions, the operator need only use his index finger to displace the actuator mechanism 30 by a little more than one-half the length of the path of travel 118, and the scalpel 20 is advantageous in this respect.

Still another advantage provided by the scalpel 20 relates to its relatively few number of components. More specifically and when compared to some common scalpel assemblies whose blades are covered by a movable blade-protecting shield, the depicted scalpel 20 has fewer components.

It follows from the foregoing that a scalpel handle-providing means (or handle) 18 has been described for holding a blade 24 having a cutting edge 44 which includes a handle member 22 and a blade shield 26 for covering, when desired, the blade cutting edge 44. The blade shield 26 is connected to the handle member 22 for pivotal movement relative thereto about a pivot axis 68 between a blade-covering position and an out-of-the-way position. A finger-operable actuator mechanism 30 is mounted upon the handle member 22 for sliding movement relative thereto between a first (i.e. rearwardly-disposed) condition and a second (i.e. forwardly-disposed) condition, and an over center spring 25 is interposed between the actuator mechanism 30 and the handle member 22 so that upon movement of the actuator mechanism 30 from its first condition into the position assumed by the actuator mechanism 30 when in its second condition, the blade shield 26 is biased by the over center spring 25 (by way of the actuator mechanism 30) into the out-of-the-way position. Furthermore and upon movement of the actuator mechanism 30 from its second condition into the position assumed by the actuator mechanism 30 when in its first condition, the blade shield 26 is biased by the over center spring 25 (by way of the actuator mechanism 30) into the blade-covering position.

It will be understood that numerous modifications and substitutions can be had to the aforedescribed embodiment 20 without departing from the spirit of the invention. Accordingly, the aforedescribed embodiment 20 is intended for the purpose of illustration and not as limitation.

The invention claimed is:

1. A scalpel handle for holding a blade having a cutting edge, the scalpel handle comprising:
   a handle member to which a blade is securable for use;
   a blade shield for covering the cutting edge of the blade when the blade is secured to the handle member wherein the blade shield is connected to the handle member for movement relative thereto between a blade-covering position at which the blade shield covers the cutting edge of the blade and an out-of-the way position at which the cutting edge of the blade is exposed for use;
   a manually-operable actuator mechanism which is mounted upon the handle member for movement relative thereto between a first condition and a second condition and along a substantially linear path of movement; and
   the actuator mechanism is connected to the blade shield so that by manually moving the actuator mechanism from the first condition toward the second condition, the blade shield is moved from the blade-covering position toward the out-of-the-way position and so that by manually moving the actuator mechanism from the second condition toward the first condition, the blade shield is moved from the out-of-the way position toward the blade-covering position; and an over center spring having two opposite end portions and being interposed between the actuator mechanism and the handle member so that upon movement of the actuator mechanism from the first condition into the position assumed by the actuator mechanism when in the second condition, the blade shield is biased by the over center spring into the out-of-the-way position and the over center spring resists movement of the actuator mechanism out of the second condition and toward the position assumed by the actuator mechanism when in the first condition, and so that upon movement of the actuator mechanism from the second condition into the position assumed by the actuator mechanism when in the first condition, the blade shield is biased by the over center spring into the blade-covering position and the over center spring resists movement of the actuator mechanism from the first condition toward the position assumed by the actuator mechanism when in the second condition wherein one end portion of the over center spring is adapted to act against the actuator mechanism and the other end portion of the over center spring is adapted to act against the handle member when the actuator mechanism is moved between the first and second conditions, and the one end portion of the over center spring cooperates with the actuator mechanism so that as the actuator mechanism is moved between the first condition and the second condition and along the substantially linear path of movement, the one end portion of the over center spring also moves along a substantially linear path of movement; and wherein one of the actuator mechanism and the handle member includes a tab portion and the other of the actuator mechanism and the handle member includes a guide track along which the tab portion is slidably received so that as the actuator mechanism is moved relative to the handle member between the first and second conditions, the actuator mechanism is moved along the substantially linear path of movement as the tab portion is guided along the guide track; and wherein the over center spring is adapted to pivot about one of the two end portions of the over center spring when the actuator mechanism is moved between the first condition and the second condition.

2. The scalpel handle as defined in claim 1 wherein the actuator mechanism is adapted to move in a first direction along the substantially linear path of movement when the actuator mechanism is moved from the first condition toward the second condition, and wherein the over center spring is adapted to act between the actuator mechanism and the handle member so that until the actuator mechanism is moved in the first direction along the path of movement toward the second condition by a predetermined interval, the over center spring opposes the movement of the actuator mechanism in the first direction but upon movement of the actuator mechanism in the first direction along the substantially linear path of movement beyond the predetermined interval, the over center spring biases the blade shield into the out-of-the-way position.

3. The scalpel handle as defined in claim 2 wherein the substantially linear path of movement along which the actuator mechanism is adapted to move is a first path of movement and the actuator mechanism is adapted to move relative to the handle member from a first limit of travel to a second limit of travel as the actuator mechanism is moved along the first path of movement from the first condition to the second condition and the first path of movement has a midpoint located substantially midway between the first and second limits of travel, and the predetermined interval substantially corresponds with the distance moved by the actuator mechanism from the first condition to the midpoint of the first path of movement.

4. The scalpel handle as defined in claim 1 wherein the substantially linear path of movement along which the actuator mechanism is adapted to move is a first path of movement and the actuator mechanism is mounted upon the handle member for movement relative thereto from the first condition to the second condition along the first path of movement and between first and second limits of travel, and the first path of movement has a midpoint located substantially midway along the length of the first path of movement, and the over center spring is adapted to act between the actuator mechanism and the handle member so that until the actuator mechanism has been moved from the first condition along the first path of movement to about the midpoint of the first path of movement, the movement of the blade shield toward the out-of-the-way position is opposed by the biasing force of the over center spring, but upon movement of the actuator mechanism from the first condition along the first path of movement beyond the midpoint of the first path of movement, the blade shield is biased toward the out-of-the-way position by the biasing force of the over center spring.

5. The scalpel handle as defined in claim 1 wherein the over center spring has a major portion which extends between the two opposite end portions which is substantially C-shaped in form.

6. The scalpel handle as defined in claim 1 wherein the over center spring is mounted within the handle member so that upon movement of the actuator mechanism to the second condition, the over center spring is in a compressed condition which biases the opposite end portions of the spring further apart to thereby bias the blade shield into the out-of-the-way position.

7. A scalpel handle for holding a blade having a cutting edge, the scalpel handle comprising:
    a handle member to which a blade is securable for use;
    a blade shield for covering the cutting edge of the blade when the blade is secured to the handle member wherein the blade shield is connected to the handle member for movement relative thereto between a blade-covering position at which the blade shield covers the cutting edge of the blade and an out-of-the way position at which the cutting edge of the blade is exposed for use;
    a manually-operable actuator mechanism which is mounted upon the handle member for movement relative thereto between a first condition and a second condition and along a first substantially linear path of movement; and
    the actuator mechanism is connected to the blade shield so that by manually moving the actuator mechanism from the first condition toward the second condition, the blade shield is moved from the blade-covering position toward the out-of-the-way position and so that by manually moving the actuator mechanism from the second condition toward the first condition, the blade shield is moved from the out-of-the-way position toward the blade-covering position; and an over center spring having two opposite end portions and being interposed between the actuator mechanism and the handle member so that upon movement of the actuator mechanism from the first condition into the position assumed by the actuator mechanism when in the second condition, the blade shield is biased by the over center spring into the out-of-the-way position and the action of the over center spring resists movement of the actuator mechanism out of the second condition and toward the position assumed by the actuator mechanism when in the first condition, and so that upon movement of the actuator mechanism from the second condition into the position assumed by the actuator mechanism when in the first condition, the blade shield is biased by the over center spring into the blade-covering position and the action of the over center spring resists movement of the actuator mechanism out of the first condition and toward the position assumed by the actuator mechanism when in the second condition wherein one end portion of the over center spring is adapted to act against the actuator mechanism and the other end portion of the over center spring is adapted to act against the handle member when the actuator mechanism is moved between the first and second conditions, and the one end portion of the over center spring cooperates with the actuator mechanism so that as the actuator mechanism is moved between the first condition and the second condition and along the first substantially linear path of movement, the one end portion of the over center spring also moves along a substantially linear path of movement; and wherein one of the actuator mechanism and the handle member includes a tab portion and the other of the actuator mechanism and the handle member includes a guide track along which the tab portion is slidably received so that as the actuator mechanism is moved relative to the handle member between the first and second conditions, the actuator mechanism is moved along the first substantially linear path of movement as the tab portion is guided along the guide track; and wherein the over center spring is adapted to pivot about one of the two end portions of the over center spring when the actuator mechanism is moved between the first condition and the second condition.

8. The scalpel handle as defined in claim 7 wherein the over center spring is mounted within the scalpel handle so that when the actuator mechanism is moved into the second condition from the first condition or into the first condition from the second condition, the spring is in a compressed condition which biases the opposite end portions of the over center spring further apart.

9. The scalpel handle as defined in claim 7 wherein the actuator mechanism is adapted to move along the first path of movement as the actuator mechanism is moved between the first condition and the second condition wherein the actuator mechanism is adapted to move in a first direction along the first path of movement when the actuator mechanism is moved from the first condition toward the second condition and is adapted to move in a second direction along the first path of movement when the actuator mechanism is moved from the second condition toward the first condition, and wherein the over center spring is adapted to act between the actuator mechanism and the handle member so that until the actuator mechanism is moved in the first direction along the first path of movement toward the second condition by a predetermined interval, the over center spring opposes the movement of the actuator mechanism in the first direction but upon movement of the actuator mechanism in the first direction along the first path of movement beyond the predetermined interval, the over center spring biases the blade shield into the out-of-the-way position and so that until the actuator mechanism is moved in the second direction along the first path of movement toward the first condition by a predetermined distance, the over center spring opposes the movement of the actuator mechanism in the second direction but upon movement of the actuator mechanism in the second direction along the first path of movement beyond the predetermined distance, the over center spring biases the blade shield into the blade-covering position.

10. The scalpel handle as defined in claim 9 wherein the actuator mechanism is adapted to move relative to the handle member along the first path of movement between a first limit of travel and a second limit of travel as the actuator mechanism is moved between the first condition and the second condition and the first path of movement has a midpoint located substantially midway between the first and second limits of travel, and the predetermined interval substantially corresponds with the distance moved by the actuator mechanism in the first direction from the first condition to the midpoint of the path of movement and the predetermined distance substantially corresponds with the distance moved by the actuator mechanism in the second direction from the second condition to the midpoint of the first path of movement.

11. The scalpel handle as defined in claim 7 wherein the actuator mechanism is mounted upon the handle member for movement relative thereto between the first condition and the second condition along the first path of movement and between first and second limits of travel, and the first path of movement has a midpoint located substantially midway along the length of the first path of movement, and the over center spring is adapted to act between the actuator mechanism and the handle member so that until the actuator mechanism has been moved from the first condition toward the second condition along the first path of movement to about the midpoint of the first path of movement, the movement of the blade shield toward the out-of-the-way position is opposed by the biasing force of the over center spring, but upon movement of the actuator mechanism from the first condition toward the second condition along the first path of movement beyond the midpoint of the first path of movement, the blade shield is biased toward the out-of-the-way position by the biasing force of the over center spring and so that until the actuator mechanism has been moved from the second condition toward the first condition along the first path of movement to about the midpoint of the first path of movement, the movement of the blade shield toward the blade-covering position is opposed by the biasing force of the over center spring, but upon movement of the actuator mechanism from the second condition toward the first condition along the first path of movement beyond the midpoint of the first path of movement, the blade shield is biased toward the blade-covering position by the biasing force of the over center spring.

12. The scalpel handle as defined in claim 7 wherein the over center spring is mounted within the scalpel handle so that upon movement of the actuator mechanism into the second condition, the over center spring is disposed in a compressed condition which biases the two end portions of the spring apart and thus biases the actuator mechanism into the second condition and so that upon movement of the actuator mechanism into the first condition, the over center spring is disposed in a compressed condition which biases the two end portions of the spring apart and thus biases the actuator mechanism into the first condition.

13. The scalpel handle as defined in claim 12 wherein the actuator mechanism is mounted for movement relative to the handle member along the first substantially linear path of movement between a first limit of travel which corresponds to the first condition of the actuator mechanism and a second limit of travel which corresponds to the second condition of the actuator mechanism, and the first path of movement has a midpoint which is located substantially between the first and second limits of travel and said one end of the two opposite ends of the spring is adapted to act against the handle member at a preselected location thereon wherein said preselected location is closest to the first path of movement at the midpoint thereof so that when the actuator mechanism is disposed at any location along the first path of movement between the midpoint thereof and the second condition, the compressed condition of the spring acts through the actuator mechanism to bias the blade shield toward the out-of-the-way position and so that when the actuator mechanism is disposed at any location along the first path of movement between the midpoint thereof and the first condition, the compressed condition of the spring acts through the actuator mechanism to bias the blade shield toward the blade-covering position.

14. A scalpel assembly comprising:
a blade having a cutting edge;
a handle member to which the blade is secured;
a blade shield for covering the cutting edge of the blade wherein the blade shield is connected to the handle member for movement relative thereto between a blade-covering position at which the blade shield covers the cutting edge of the blade and an out-of-the way condition at which the cutting edge of the blade is exposed for use;
a manually-operable actuator mechanism which is mounted upon the handle member for movement relative thereto between a first condition and a second condition and along a first substantially linear path of movement; and
the actuator mechanism is connected to the blade shield so that by manually moving the actuator mechanism from the first condition toward the second condition, the blade shield is moved from the blade-covering position toward the out-of-the-way position and so that by manually moving the actuator mechanism from the second condition toward the first condition, the blade shield is moved from the out-of-the-way position toward the blade-covering position; and an over center spring having two opposite end portions and being interposed between the actuator mechanism and the handle member so that upon movement of the actuator mechanism from the first condition into the position assumed by the actuator mechanism when in the second condition, the blade shield is biased by the over center spring into the out-of-the-way position and the over center spring resists movement of the actuator mechanism out of the second condition and toward the position assumed by the actuator mechanism when in the first condition, and so that upon movement of the actuator mechanism from the second condition into the position assumed by the actuator mechanism when in the first condition, the blade shield is biased by the over center spring into the blade-covering position and the over center spring resists movement of the actuator mechanism from the first condition toward the position assumed by the actuator mechanism when in the second condition wherein one end portion of the over center spring is adapted to act against the actuator mechanism and the other end portion of the over center spring is adapted to act against the handle member when the actuator mechanism is moved between the first and second conditions, and the one end portion of the over center spring cooperates with the actuator mechanism so that as the actuator mechanism is moved between the first condition and the second condition and along the first substantially linear path of movement, the one end portion of the over center spring also moves along a substantially linear path of movement; and wherein one of the actuator mechanism and the handle member includes a tab portion and the other of the actuator mechanism and the handle member includes a guide track along which the tab portion is slidably received so that as the actuator mechanism is moved relative to the handle member between the first and second conditions, the actuator mechanism is moved along the first substantially linear path of movement as the tab portion is guided along the guide track; and wherein the over center spring is adapted to pivot about one of the two end portions of the over center spring when the actuator mechanism is moved between the first condition and the second condition.

* * * * *